US010147175B2

(12) United States Patent
Bahgat Shehata et al.

(10) Patent No.: US 10,147,175 B2
(45) Date of Patent: Dec. 4, 2018

(54) DETECTION OF HARDWARE TROJAN USING LIGHT EMISSIONS WITH SACRIFICIAL MASK

(71) Applicant: INTERNATIONAL BUSINESS MACHINES CORPORATION, Armonk, NY (US)

(72) Inventors: Andrea Bahgat Shehata, White Plains, NY (US); Peilin Song, Lagrangeville, NY (US); Franco Stellari, Waldwick, NJ (US); Alan J. Weger, Mohegan Lake, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 130 days.

(21) Appl. No.: 15/414,569

(22) Filed: Jan. 24, 2017

(65) Prior Publication Data

US 2018/0211377 A1 Jul. 26, 2018

(51) Int. Cl.
*G06K 9/00* (2006.01)
*G06T 7/00* (2017.01)
(Continued)

(52) U.S. Cl.
CPC ....... *G06T 7/0004* (2013.01); *G01N 21/9501* (2013.01); *G01N 21/95607* (2013.01);
(Continued)

(58) Field of Classification Search
CPC ............... G06T 7/0004; G06T 11/20; G06T 2207/30148; G06K 9/6267;
(Continued)

(56) References Cited

U.S. PATENT DOCUMENTS 5,532,174 A 7/1996 Corrigan
5,940,545 A 8/1999 Kash et al.
(Continued)

OTHER PUBLICATIONS

B. Zhou et al., "Detecting Hardware Trojans Using Backside Optical Imaging of Embedded Watermarks," 52nd Annual Design Automation Conference (DAC), San Francisco, CA, Jun. 2015, pp. 111-116.

(Continued)

*Primary Examiner* — Phuoc Tran
(74) *Attorney, Agent, or Firm* — Intelletek Law Group, PLLC; Gabriel Daniel, Esq.

(57) ABSTRACT

A computer-implemented device and method for identifying hardware Trojans and defects based on light emissions from Integrated Circuits (ICs) is provided. A measured emissions map is received based on light emissions captured from a sacrificial test IC. The sacrificial test IC is a partially manufactured IC fabricated to include a set of frontend layers of an IC architecture but not a set of backend layers of the IC architecture. The sacrificial test IC also includes a sacrificial layer for powering devices in the partially manufactured IC without the set of backend layers. An expected emissions map is derived from the sacrificial test IC and the measured emissions map is compared with the expected emissions map to identify deviations from the IC architecture in the frontend layers.

20 Claims, 11 Drawing Sheets

(51) Int. Cl.
*H01L 23/00* (2006.01)
*H01L 21/66* (2006.01)
*G06T 11/20* (2006.01)
*G06K 9/62* (2006.01)
*G01N 21/956* (2006.01)
*G01N 21/95* (2006.01)

(52) U.S. Cl.
CPC ............ *G06K 9/6267* (2013.01); *G06T 11/20* (2013.01); *H01L 22/30* (2013.01); *H01L 23/57* (2013.01); *G01N 2201/13* (2013.01); *G06T 2207/30148* (2013.01)

(58) Field of Classification Search
CPC .......... G01N 21/9501; G01N 21/95607; H01L 22/30; H01L 23/57
See application file for complete search history.

(56) References Cited

U.S. PATENT DOCUMENTS

| | | | |
|---|---|---|---|
| 7,737,020 B1* | 6/2010 | Ho | H01L 21/76801 257/522 |
| 8,115,170 B2 | 2/2012 | Stellari et al. | |
| 8,341,759 B2 | 12/2012 | Gross et al. | |
| 9,075,106 B2 | 7/2015 | Bernstein et al. | |
| 9,618,561 B2* | 4/2017 | Meinhold | B81B 7/02 |

OTHER PUBLICATIONS

F. Stellari et al., "Functional Block Extraction for Hardware Security Detection Using Time-Integrated and Time-Resolved Emission Measurements," 32nd VLSI Test Symposium (VTS), Napa, CA, Apr. 2014, 6 pages.

F. Stellari et al., "Testing and Diagnostics of Cmos Circuits Using Light Emission from Off-State Leakage Current," IEEE Transactions on Electron Devices, vol. 51, No. 9, Sep. 2004, pp. 1455-1462.

P. Song et al., "Counterfeit IC Detection Using Light Emission," IEEE International Test Conference (ITC), Oct. 2014, Seattle, WA, 8 pages.

P. Song et al., "MARVEL—Malicious Alteration Recognition and Verification by Emission of Light," IEEE International Symposium on Hardware-Oriented Security and Trust (HOST), Jun. 2011, San Diego, CA, pp. 117-121.

R. Adato et al., "Rapid Mapping of Digital Integrated Circuit Logic Gates Via Multi-Spectral Backside Imaging," arXiv preprint arXiv:1605.09306, May 30, 2016.

* cited by examiner

DETECTION OF HARDWARE TROJAN USING LIGHT EMISSIONS WITH SACRIFICIAL MASK

BACKGROUND

Technical Field

The present disclosure generally relates to fabrication of integrated circuits (ICs) and detection of defects during the manufacturing process of the ICs.

Description of the Related Art

The IC fabrication process generally includes two portions. The first portion of the fabrication process, referred to as front end of line (FEOL), is where the individual devices (such as transistors, capacitors, resistors, etc.,) are patterned. The FEOL generally covers everything up to the deposition of metal interconnect layers. The second portion of the fabrication process, referred to as back end of line (BEOL), is where the individual devices are interconnected with wiring on the wafer using the metallization layers.

SUMMARY

Some embodiments of the disclosure provide a computing device configured to implement a machine for designing a sacrificial layer for detecting hardware Trojans and other defects in ICs. The computing device receives an IC architecture that comprises a set of frontend layers and a set of backend layers. The computing device generates an architecture of a sacrificial layer based on the architecture of the IC, the sacrificial layer specifying power and ground connections to partially constructed devices in a partially manufactured IC that includes the set of frontend layers but not the set of backend layers. The computing device then generates an expected emissions map by simulating light emissions from the partially constructed devices based on power and ground connections provided by the sacrificial layer.

Some embodiments of the disclosure provide an apparatus configured to fabricate a sacrificial test IC with a sacrificial layer for detecting hardware Trojans and other defects. The apparatus receives a partially manufactured IC fabricated according to an IC architecture. The partially manufactured IC is fabricated to include a set of frontend layers of the IC architecture but not a set of backend layers of the IC architecture. The apparatus receives an architecture of a sacrificial layer and processes the partially manufactured IC to include the sacrificial layer by providing conducting material according to the architecture of the sacrificial layer to connect partially constructed devices in the partially manufactured IC to power and ground. The apparatus outputs the partially manufactured IC with the sacrificial layer as a sacrificial test IC.

Some embodiments of the disclosure provide a computer-implemented method for identifying hardware Trojans and defects based on light emissions from ICs. The method receives a measured emissions map based on light emissions captured from a sacrificial test IC. The sacrificial test IC is a partially manufactured IC fabricated to include a set of frontend layers of an IC architecture but not a set of backend layers of the IC architecture. The sacrificial test IC also includes a sacrificial layer for powering devices in the partially manufactured IC without the set of backend layers. The method receives an expected emissions map for the sacrificial test IC and compares the measured emissions map and the expected emissions map to identify deviations from the IC architecture in the frontend layers.

The preceding Summary is intended to serve as a brief introduction to some embodiments of the disclosure. It is not meant to be an introduction or overview of all inventive subject matter disclosed in this document. The Detailed Description that follows and the Drawings that are referred to in the Detailed Description will further describe the embodiments described in the Summary as well as other embodiments. Accordingly, to understand all the embodiments described by this document, a Summary, Detailed Description and the Drawings are provided. Moreover, the claimed subject matter is not to be limited by the illustrative details in the Summary, Detailed Description, and the Drawings, but rather is to be defined by the appended claims, because the claimed subject matter can be embodied in other specific forms without departing from the spirit of the subject matter.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION

Figure 1:
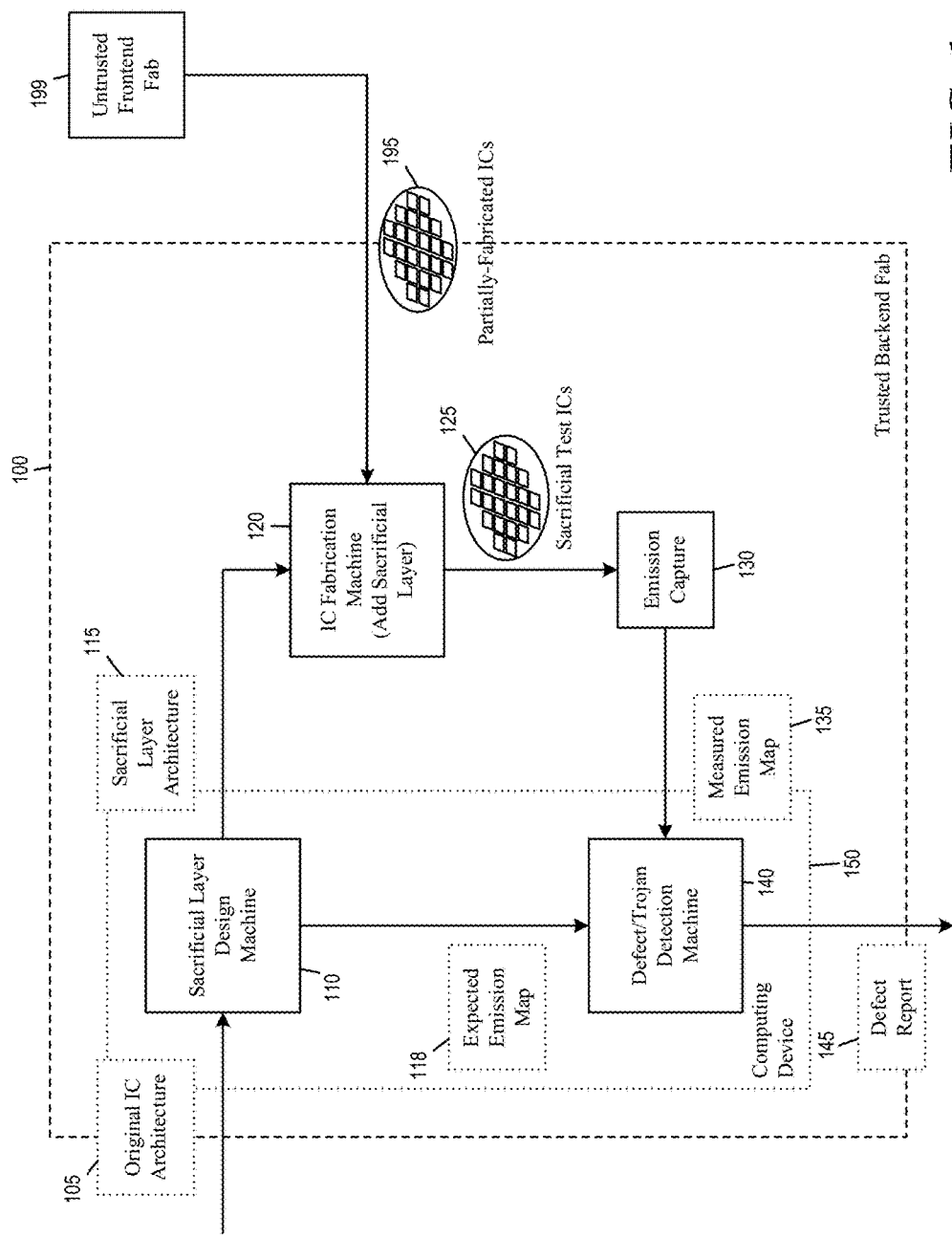
FIG. 1 illustrates an example trusted facility that processes integrated circuits (ICs) to include a sacrificial layer in order to detect hardware Trojans and defects by light emissions.

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

Under the trend of globalization, integrated circuits (ICs) that are designed in one country under the trusted environment could be manufactured in a fab that resides in another country where the process could not be fully trusted. An untrusted fab may introduce hardware alterations, also referred to as "Trojans," into the ICs that are manufactured at the facility. Such Trojans may alter the ICs' functionality or negatively impact the ICs' reliability.

To make sure the fabrication process of the ICs is trusted and secure, a technique called "split manufacturing" is being studied and developed, especially by the U.S. government. In split manufacturing, the first portion of the fabrication process, known as front end of line (FEOL), is performed at an untrusted fab, while the second portion of the fabrication process, known as back end of line (BEOL) is processed in the trusted fab after FEOL is completed. A final manufacturing test is performed after the ICs are fully built. The idea behind this approach is to secure the manufacturing of the ICs through the BEOL such that the ICs are fabricated according to their original architectures. An original architecture of an IC specifies what devices are authorized to exist in the IC (authorized devices). An IC fabricated according to its original architecture should not have any unauthorized devices inserted, any authorized devices omitted, or any doping profiles altered. Although this methodology significantly increases the chance of Trojan detection, certain type of Trojans, especially the reliability Trojans, cannot be easily detected. Furthermore, waiting until the ICs are fully built to detect certain types of Trojans may be too late or too costly.

Some embodiments of the disclosure provide a method of testing an IC that is partially manufactured (i.e., partially fabricated) at an untrusted fab to only include frontend layers. The method detects hardware Trojans and other defects in the IC by designing a sacrificial layer mask. The partially manufactured IC is processed up to the sacrificial layer at the trusted fab to create a sacrificial test IC. The sacrificial layer provides connections to bring power and ground to each authorized device in the sacrificial test IC. After powering up the sacrificial test IC, light emissions from the sacrificial test IC is captured and measured, and the method identifies Trojans and other defects based on the measured emissions. The method also uses the sacrificial layer to set device inputs in the sacrificial test IC in order to produce specified emissions patterns. The method uses light emissions from the sacrificial test IC to detect hardware Trojans and defects that may be introduced by the untrusted fab, Trojans such as omitted devices, unauthorized devices, and altered doping profiles.

FIG. 1 illustrates an example trusted facility 100 that processes ICs to include a sacrificial layer in order to detect hardware Trojans and defects by light emissions. The trusted facility is a backend fab that receives a batch of partially manufactured/fabricated ICs 195 from an untrusted frontend fab 199. In some embodiments, the backend fab receives the batch of partially manufactured ICs as dies on a wafer delivered from the frontend fab. The trusted backend fab processes some of the received partially manufactured ICs to include the sacrificial layer to create sacrificial test ICs. The sacrificial layer provides power and ground connections to the devices (gates, transistors, memories, etc.,) in the sacrificial test ICs so the devices would emit light. The backend facility uses the light emissions from the sacrificial test ICs to detect Trojans and other defects that may be introduced by the untrusted frontend fab 199.

As illustrated, the trusted fab 100 has four machines for implementing Trojan detection based on a sacrificial layer: a sacrificial layer design machine 110, an IC fabrication machine 120, an emissions capture machine 130, and a defect/Trojan detection machine 140. The sacrificial layer design machine 110 receives an original architecture specification 105 and generates a sacrificial layer architecture 115 and an expected emissions map 118. The IC fabrication machine 120 receives the sacrificial layer architecture 115 and processes some of the partially manufactured ICs 195 to include the sacrificial layer to create sacrificial test ICs 125. The emissions capture machine 130 provides power to the sacrificial test ICs and captures the ICs' light emissions to generate a measured emissions map 135. The defect/Trojan detection machine 140 compares the measured emissions map 135 with the expected emissions map 118 and generates a defect report 145.

The machines 110, 120, 130, and 140 of the trusted facility 100 may be located at the same physical facility or at different physical facilities. These four machines may also be implemented as one physical machine. In some embodiments, the emissions capture machine 130 is built into the defect detection machine 140 as a component therein. In some embodiments, the sacrificial layer design machine 110 and the defect detection machine 140 are implemented by a same computing device 150, while the IC fabrication machine 120 and the emissions capture machine 130 are physically distinct machines. In some embodiments, the sacrificial layer design machine 110 and the defect/Trojan detection machine 140 are implemented by data processing systems described later in the context of FIG. 11 below.

The sacrificial layer design machine 110 is configured to specify the architecture of the sacrificial layer. The specification is made based on the original architecture specification 105, which specifies the design (e.g., layout patterns, dimensions, electrical connections) of all process layers of the IC. The original architecture specification 105 includes the architectures of all devices (i.e., gates, memories, transistors, registers, mix signal components, etc.,) on the IC. These are the authorized devices that the designers of the IC intend to be present on the IC when the IC is without any Trojans or defects. Based on the original architecture specification 105, the sacrificial layer design machine 110 provides an architecture of the sacrificial layer that brings power and ground to the authorized devices without using any of the processing layers above the sacrificial layer. The sacrificial layer design machine 110 also performs simulation based on the sacrificial layer architecture to predict/compute the intensities of light emissions from the devices of the sacrificial test IC. The sacrificial layer design machine 110 generates the expected emissions map 118 based on the simulated light intensities.

In some embodiments, the sacrificial layer design machine 110 automatically specifies the ground and power connections based on the locations of the devices in the original architecture specification. In some embodiments, the sacrificial layer design machine 110 provides a user interface that allows an engineer to manually specify at least some of the ground and power connections in sacrificial layer. The sacrificial layer design machine 110 also receives input specification for connecting the inputs of the devices (i.e., to either logical '1' or logical '0' by connecting to either power or ground). The architecture of the sacrificial layer is provided to the IC fabrication machine 120 as the sacrificial layer architecture 115, which specifies the design of the sacrificial layer (e.g., layout patterns, dimensions, electrical connections) as a process mask. The operations of the sacrificial layer design machine 110 are described further in the context of FIG. 8 below.

The IC fabrication machine 120 physically fabricates the IC by a sequence of photo lithographic and chemical processing steps during which electronic circuits are gradually created on a wafer made of semiconducting material. The IC fabrication machine 120 adds each processing layer of the IC architecture by depositing conducting or semi-conducting materials on the wafer according to a mask of that layer. The IC fabrication machine 120 can be configured to deposit conducting material on partially manufactured ICs 195 according to a mask of the sacrificial layer (according to the architecture 115) to create the sacrificial test ICs 125. The IC fabrication will not perform processing layers of the IC above sacrificial layer for the sacrificial test ICs. The operations of the IC fabrication machine 120 will be further described by reference to FIG. 9 below.

The defect/Trojan detection machine 140 is for identifying defects and Trojans based on the light emissions captured from the sacrificial ICs 125. In the example trusted backend fab 100, the defect/Trojan detection machine 140 receives an expected emissions map 118 from the sacrificial layer design machine 110 and uses the received map as basis for comparison with the measured emissions map 135. The defect/Trojan detection machine 140 examines the measured emissions map 135 with respect to the expected emissions map 118. In some embodiments, the defect/Trojan detection machine 140 compares the light intensity of the measured emissions map 135 with the light intensity of the expected emissions map 118. Regions in the measured emissions map having unexpected emissions (e.g., places where the differences in emissions intensities are greater than a certain threshold) are reported as possible Trojans or defects in the defect report 145. Based on this report, the trusted backend fab may reject all partially manufactured IC 195 as being infected by Trojans, or accept the partially manufactured ICs 195 as safe and proceed to fully build the remaining partially manufactured ICs (i.e., those not made into sacrificial test ICs) by completing the all processing layers of the original architecture. The sacrificial test ICs are discarded and not used for further processing after being used for Trojans detection. The operations of the defect/Trojan detection machine 140 will be further described in the context of FIG. 10 below.

Figure 2:
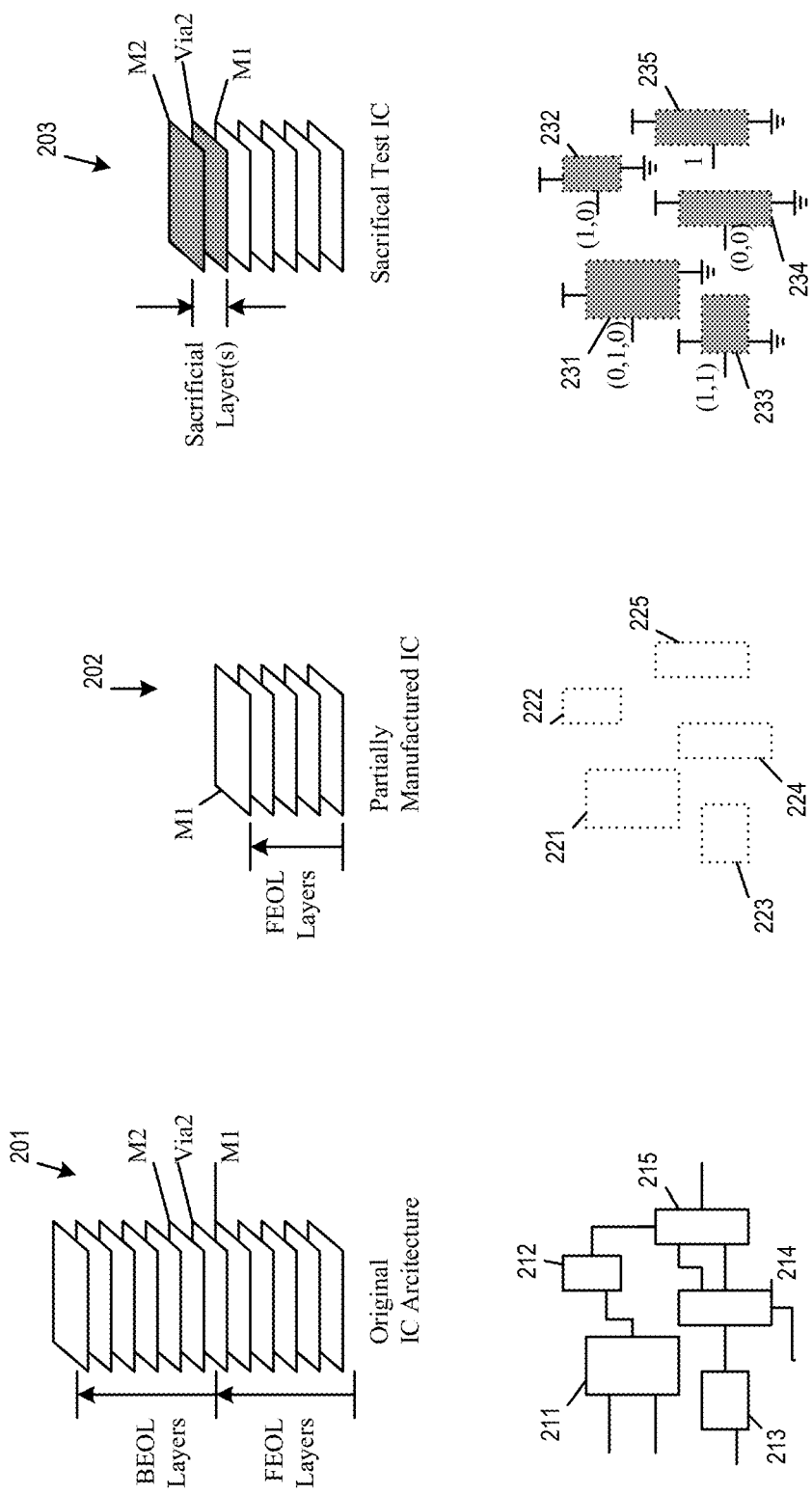
FIG. 2 illustrates the processing layers of an IC architecture at different stages of the manufacturing process, consistent with an exemplary embodiment.

FIG. 2 illustrates the processing layers of an IC architecture at different stages of the manufacturing process, consistent with an exemplary embodiment. The figure conceptually illustrates the processing layers of a fully built IC 201, a partially manufactured IC 202, and a sacrificial test IC 203. The figure also illustrates a set of fully built devices 211-215 of the fully built IC 201, a set of partially built devices 221-225 in the partially manufactured IC 202, and a set of partially built devices 231-235 with a sacrificial layer of the sacrificial test IC 203.

The fully built IC 201 has all of its processing layers according to its original architecture 201, including both FEOL layers and BEOL layers. Correspondingly, the fully built devices 211-215 in the fully built IC 201 are complete with FEOL and BEOL layers and should function as designed (barring Trojans or manufacturing defects).

The FEOL layers are built in an untrusted frontend fab (such as 199). These FEOL layers generally include all processes of CMOS fabrication to form fully isolated CMOS elements, including n-doping, p-doping, oxide, etc. The BEOL layers are built in a trusted backend fab (such as 100), where the individual devices (e.g., transistors, capacitors, resistors, etc.,) are interconnected by wiring on the wafer. BEOL includes contacts, insulating layers, metal layers, and bonding sites for chip-to-package connections. BEOL generally begins when the first or second layer of metal is deposited on the wafer. In some split manufacturing processes, the FEOL includes processing layers up to and including Metal 1 (M1), while the BEOL builds all layers thereafter, including Metal 2 (M2).

The partially manufactured IC 202 has only FEOL layers of the IC architecture. Specifically, the partially manufactured IC 202 is processed up to and including M1 but not the process layers thereafter. When an IC is only partially manufactured up to the M1 level, most or all devices in the IC are not connected to power and/or ground. As illustrated, the partially built devices 221-225 in the partially manufactured IC 202 have no access to power and ground and cannot function as designed. The partially built devices 221-225 cannot emit light because they cannot be powered up.

The sacrificial test IC 230 has one or more sacrificial layers that are built on top of the FEOL layers. The sacrificial layer(s) provide conductors at the M2 layer, as well as the Via2 layer for interconnecting M2 layer metals with the FEOL layers. The sacrificial layer brings power to the partially manufactured devices at the M2 level so these devices can power up and emit detectable light. This allows early Trojan detection at the M2 level before the IC is fully built. As illustrated, the partially built devices 231-235 have power and ground connections provided by the sacrificial layer in the sacrificial test IC 203. The devices 231-235 may not function as designed, but they can be powered up to emit detectable light. The sacrificial test IC 230 is typically built for testing purposes only and not processed further to produce a functional IC according to the IC architecture.

Figure 3:
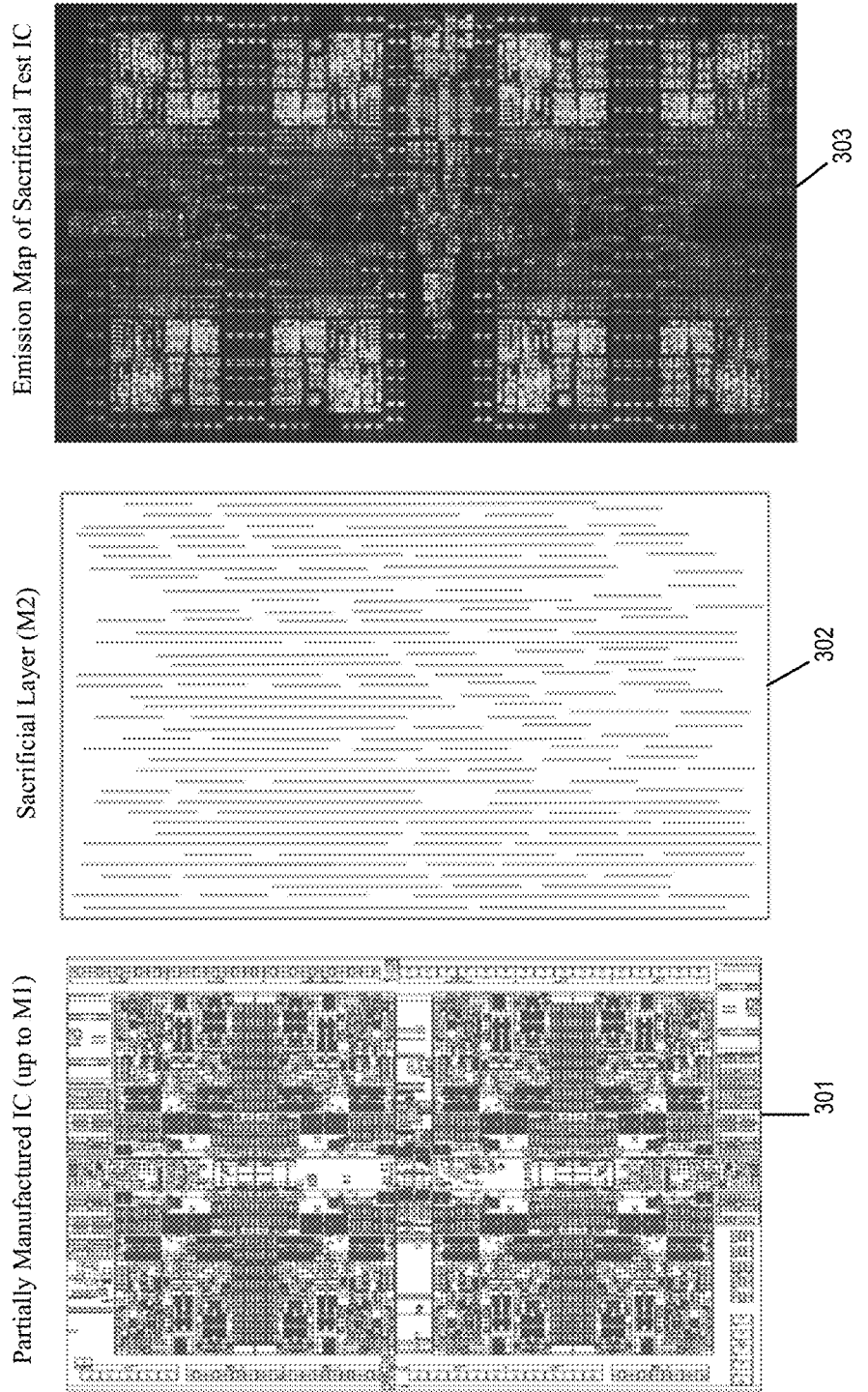
FIG. 3 shows an emissions map from a partially manufactured IC with a sacrificial layer, consistent with an exemplary embodiment.

FIG. 3 shows an emissions map from a partially manufactured IC with a sacrificial layer, consistent with an exemplary embodiment. The figure shows a partially manufactured IC 301, a sacrificial layer architecture 302, and an emissions map 303 of a sacrificial test IC. The partially manufactured IC 301 is processed up to the M1 layer at an untrusted frontend fab and is populated with partially fabricated devices. The sacrificial layer architecture 302 provides M2 level conductors the ability to power the partially fabricated devices in the partially manufactured IC 301. The emissions map 303 shows the light emissions from a sacrificial test IC that is created by processing the partially manufactured IC 301 up to the M2 level according to the sacrificial layer architecture 302. The emissions are from the partially fabricated devices in the sacrificial test IC with power and ground connections provided by the sacrificial layer 302.

Figure 4:
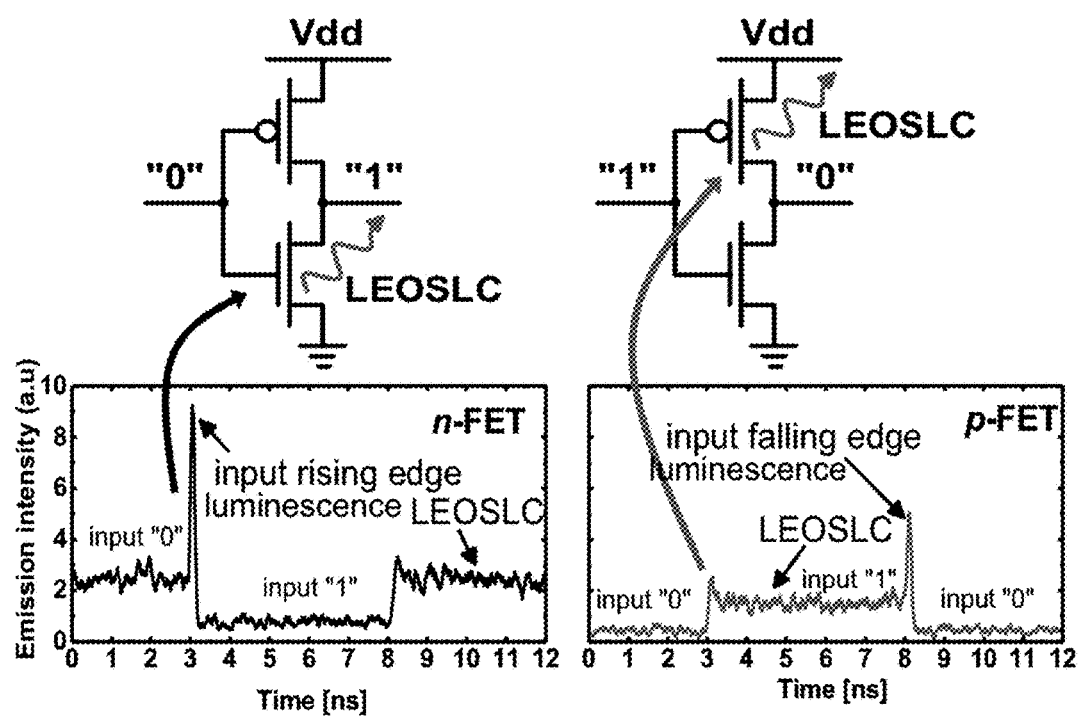
FIG. 4 shows light emissions from off-state leakage current emissions, also known as Light Emission from Off-State Leakage Current (LEOSLC), from a complementary metal oxide semiconductor (CMOS) device, consistent with an exemplary embodiment.

When a complementary metal-oxide-semiconductor (CMOS) device is powered up, it produces Light Emissions from Off-state Leakage Current (LEOSLC), also referred to as off-state leakage emission, of the CMOS field-effect transistors (FETs). FIG. 4 shows LEOSLC emissions from a CMOS device, consistent with an exemplary embodiment. The figure shows an example CMOS inverter with power connection (Vdd) and ground connection (Vss). When the input of the CMOS inverter is at logic '0' and its n-FET transistor is at off state, the n-FET transistor produces LEOSLC luminescence. Conversely, when the input of the CMOS inverter is at logic '1' and its p-FET transistor is at off state, the p-FET transistor produces LEOSLC luminescence. (The spikes of luminescence at the input rising and falling edges are not considered LEOSLC.)

Figure 5:
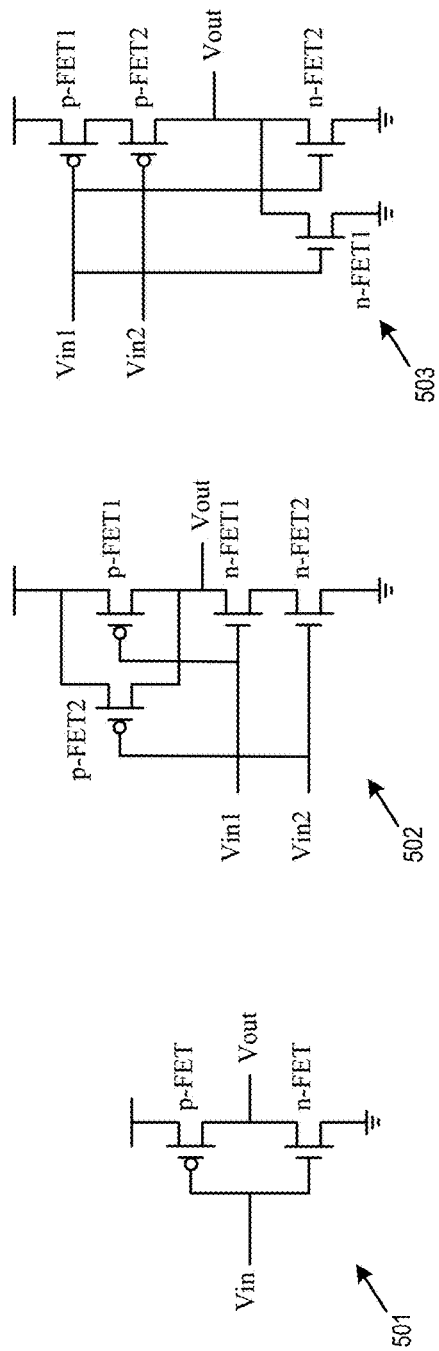
FIG. 5 illustrates emissions signatures from example CMOS devices.

FIG. 5 illustrates emissions signatures from example CMOS devices. The emissions signatures are that of an inverter 501, a NAND gate 502, and a NOR gate 503. For each CMOS gate, the figure shows a corresponding table of the gate's LEOSLC emissions at different input settings. Specifically, the figure shows a CMOS inverter emissions signature table 511, a CMOS NAND gate emissions signature table 512, and a CMOS NOR gate emissions signature table 513. Each table entry of a gate type shows which transistor of the gate is emitting LEOSLC and which transistor is "dark". In other words, different input settings to a CMOS device enables different LEOSLC luminescence from different FET transistors in the CMOS device to produce different emission signatures.

In some embodiments, the trusted backend facility 100 (at its sacrificial layer design machine 110) produces a sacrificial layer architecture that selectively ties device inputs of CMOS devices to a logic '1' or '0' in order to produce a sacrificial test IC with a specific emissions pattern. As illustrated in FIG. 2 above, the sacrificial layer (M2) not only provides connection to power and ground to the devices 231-235, but also ties the inputs of the devices 231-235 to vectors of logic '1' and logic '0' (by connecting the inputs to Vdd and/or Vss).

Figure 6:
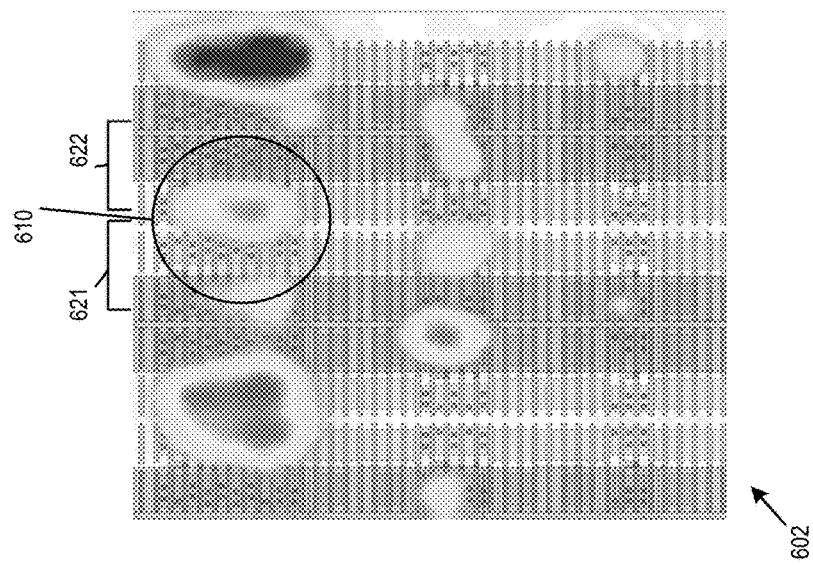
FIG. 6 shows two example emissions maps that are the results of turning ON or OFF a particular transistor by the sacrificial layer.
Figure 6:
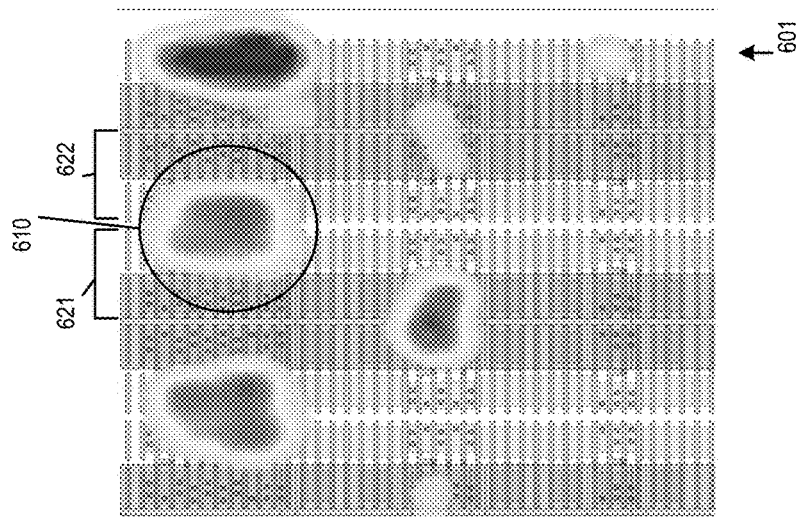

In some embodiments, the architecture of the sacrificial layer sets the inputs to the devices in the IC in a way that enhances spatial resolution of the measured emissions map. FIG. 6 shows two example emissions maps 601 and 602 that are the results of turning on or off a particular transistor by the sacrificial layer. The emissions map 601 shows a region 610 in which two adjacent gates 621 and 622 have both of their nFET transistors in their off-state so that both are producing LEOSLC emissions. The light emissions of the adjacent transistors make it difficult to distinctly identify the LEOSLC emissions of each individual device. The emissions map 602 shows the same region 610, but only the nFET transistor of the gate 622 is generating LEOSLC emissions. This is because the sacrificial layer sets the device inputs in the IC to change the state of the nFET transistor of the gate 621 to on-state (so it has no LEOSLC emissions) while leaving the nFET transistor of the gate 622 in off-state (so it has LEOSLC emissions).

Figure 7:
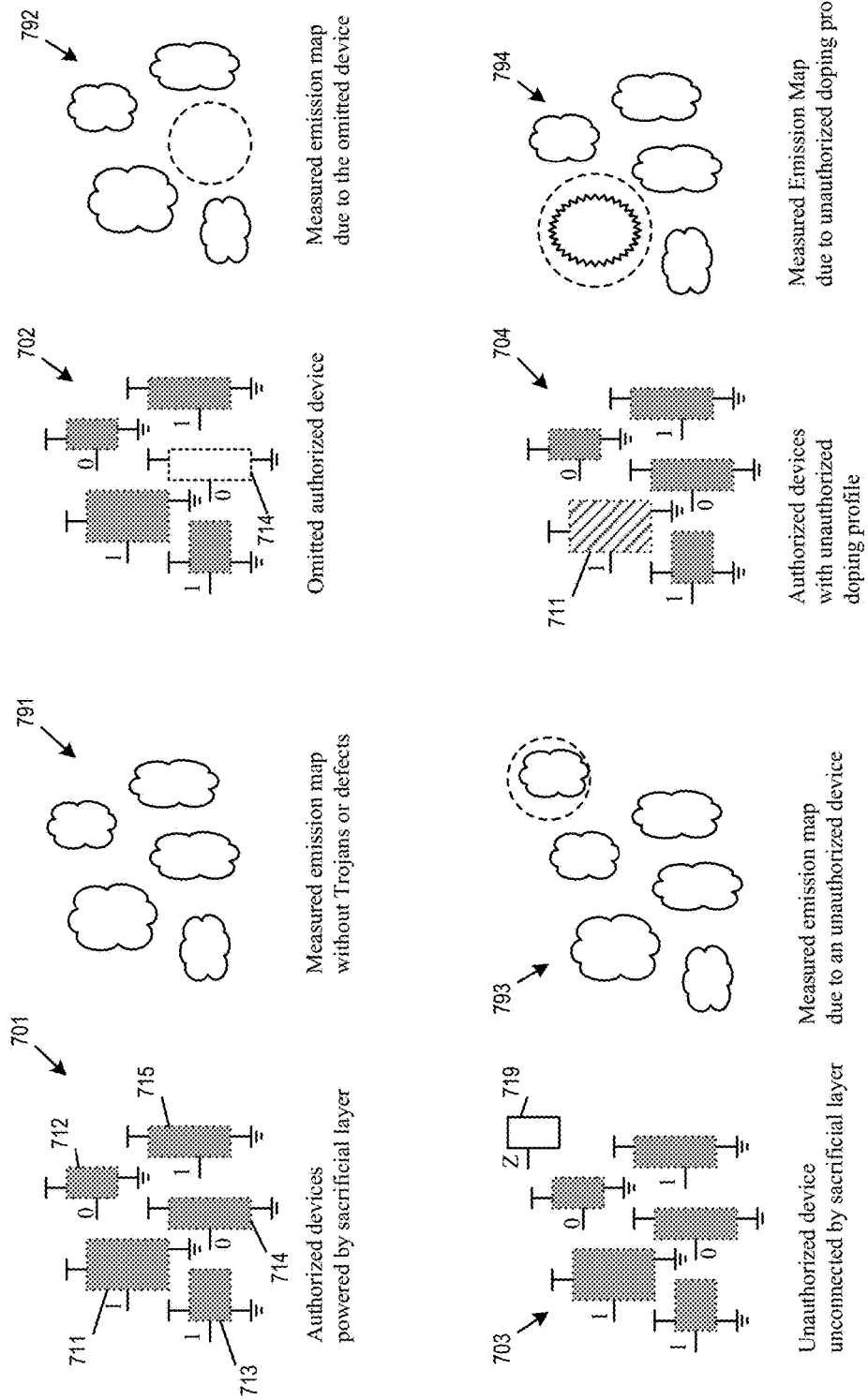
FIG. 7 illustrates the detection of different types of hardware Trojans, consistent with an exemplary embodiment.

The trusted backend fab uses the emissions measured or captured from the sacrificial test IC to identify several different types of hardware Trojans or defects in the IC. FIG. 7 illustrates the detection of different types of hardware Trojans, consistent with an exemplary embodiment. These hardware Trojans are defects in FEOL layers that deviate from the original architecture of the IC.

FIG. 7 illustrates four partially manufactured ICs 701-704 that are built according to a particular IC architecture. The FEOL layers of the partially manufactured ICs 701-704 are processed in an untrusted frontend fab, while a trusted fab has processed the partially manufactured ICs 701-704 to include the sacrificial layer (M2) according to a sacrificial layer architecture (i.e., the partially manufactured ICs 701-704 are sacrificial test ICs.) The particular IC architecture for which the sacrificial test ICs 701-704 are built, includes five devices 711-715. These five devices 711-715 are authorized devices that the designers of the IC intend to be present on the IC when the IC is without any Trojans or defects.

The figure also shows measured emissions maps 791-794 that are measured or captured from the sacrificial test ICs 701-704, respectively, when the sacrificial ICs are powered up and emits LEOSLC light. The detection of Trojans or defects is based on a comparison between the actual intensities recorded by the measured emissions map and the simulated intensities presented by the expected emissions map. Regions where the differences in emissions intensities are greater than a certain threshold are identified and reported as possible Trojans or defects.

The sacrificial test IC 701 is based on a partially manufactured IC that does not have any hardware Trojan or defects. Consequently, its corresponding measured emissions map 791 is as expected, i.e., the LEOSLC from the devices 711-715 shows no unexpected LEOSLC emissions.

The sacrificial test IC 702 has an omitted authorized device. This is a defect or a possible Trojan in the form of failure by the untrusted fab to build a device that is specified to exist in the IC, in this case the device 714. Correspondingly, the measured emissions map 792 is missing LEOSLC emissions from the device 714.

The sacrificial test IC 703 has an unauthorized device 719. This is a possible Trojan in the form of a device that is inserted into the IC by the untrusted fab. Correspondingly, the measured emissions map 793 shows unexpected LEOSLC emissions at a location that corresponds to the unauthorized device 719. In fact, in order to work properly as a Trojan, the unauthorized device 719 may receive power from unauthorized FEOL connections to other authorized devices nearby, thus generating LEOSLC when those authorized devices are powered on by the sacrificial layer. The unauthorized device 719 may also have floating inputs (logic level 'Z') that are left unconnected by the sacrificial layer, since the architecture of the sacrificial layer has no knowledge of the unauthorized device. A device having floating inputs has specific emissions signatures that are detectable by the defect/Trojan detection machine 140.

The sacrificial test IC 704 has a device whose doping profile is altered. A transistor having an altered doping profile may have an altered threshold voltage (VT), resulting in bias temperature instability (BTI) stress that may reduce the IC's usable lifetime. A doping profile alteration is therefore also referred to as a reliability Trojan. A transistor whose doping profile is altered would still pass typical manufacturing test, but would have a LEOSLC signature that is different from a properly doped transistor. (This is because LEOSLC emissions strongly depend on transistor threshold voltage.) The defect/Trojan detection machine 140 is therefore able to identify reliability Trojans from the sacrificial test IC's emissions pattern. In this case, the doping profile of the device 711 is altered, resulting in unexpected LEOSLC signature at the location of the device 711.

Figure 8:
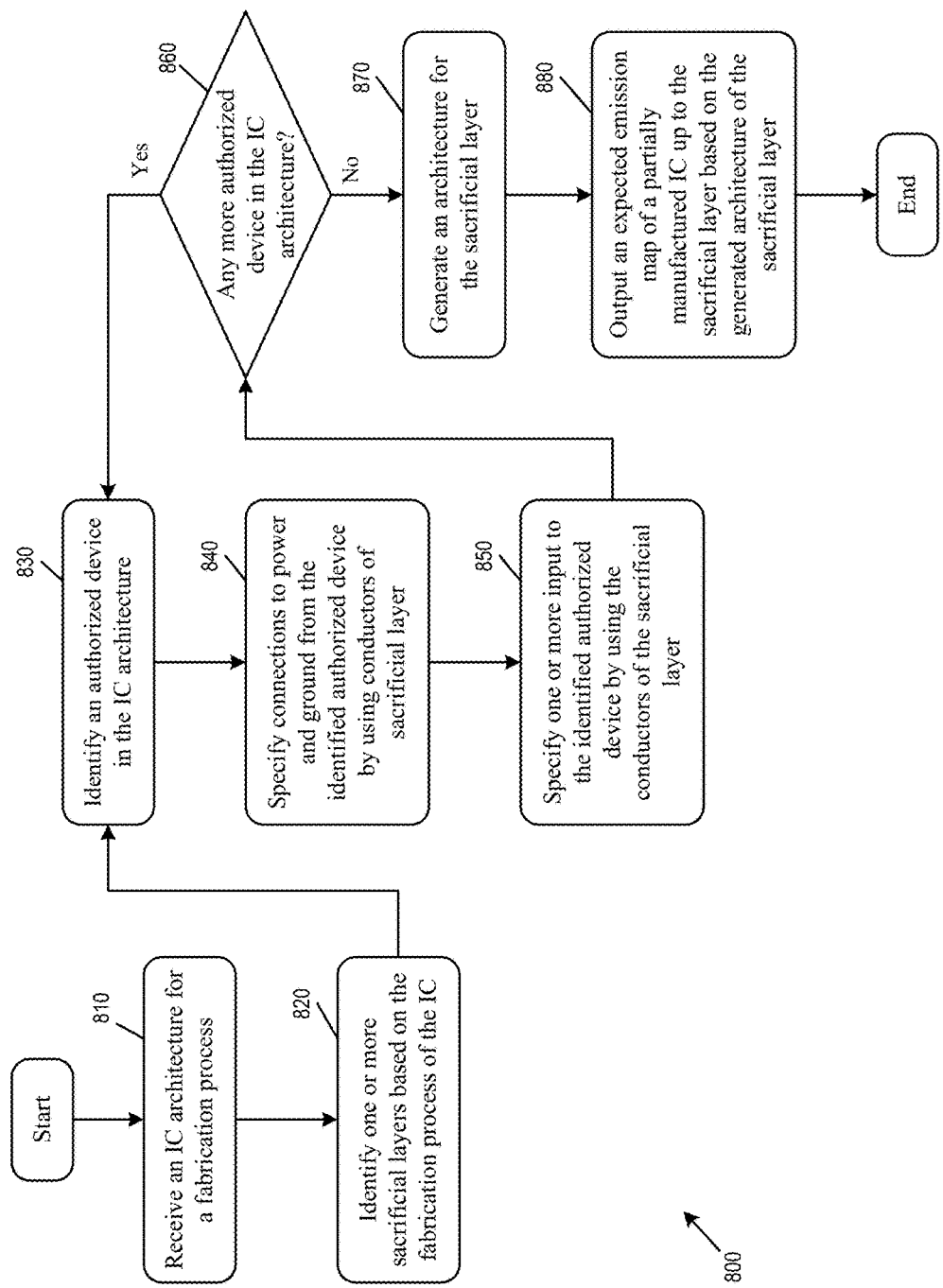
FIG. 8 conceptually illustrates a process for producing an architecture of a sacrificial layer and for producing an expected emissions map for a split manufacturing process, consistent with an exemplary embodiment.

FIG. 8 conceptually illustrates a process 800 for producing an architecture of a sacrificial layer and for producing an expected emissions map for a split manufacturing process, consistent with an exemplary embodiment. In some embodiments, one or more processing units of a computing device implementing the sacrificial layer design machine 110 at the trusted backend fab performs the process 800. The architecture of a sacrificial layer is also described in the context of FIGS. 2-6 above.

The sacrificial layer design machine starts the process 800 when it receives (at 810) an IC architecture for a fabrication process. The architecture of the IC specifies the designs (e.g., layout patterns, dimensions, electrical connections) for various processing layers of the IC as process masks under a particular technology (e.g., 22 nm, 14 nm, 10 nm, etc.) This architecture is assumed to be the original architecture of the IC as intended by its designer without any Trojans or defects.

The sacrificial layer design machine identifies (at 820) a sacrificial layer based on the fabrication process of the IC. As mentioned, the sacrificial layer is built over the FEOL layers. The sacrificial layer design machine therefore identifies the first interconnect metal layer after the FEOL layers as the sacrificial layer. In some embodiments, this sacrificial layer is M2 (along with Via2 for connecting the M2 conductors to the FEOL layers).

The sacrificial layer design machine identifies (at 830) an authorized device in the IC architecture and specifies (at 840) connections to power and ground from the identified authorized device by using conductors of the sacrificial layer. The sacrificial layer design machine also specifies (at 850) one or more inputs to the identified authorized device by specifying connections from the inputs of the device to power and/or ground by using conductors of the sacrificial layer.

Next, the sacrificial layer design machine determines (at 860) whether there are any more authorized devices in the IC architecture. If so, the process returns to 830. If the sacrificial layer design machine has specified the power, ground, and input connections of all authorized devices in the IC architecture, the process 800 proceeds to 870.

At 870, the process generates a specification for the architecture of the sacrificial layer, which may include mask(s) of the processing layer (e.g., a M2 layer mask and a Via2 layer mask). The process also outputs (at 880) an expected emissions map of the sacrificial test IC (i.e., a partially manufactured IC processed to include the sacrificial layer based on the architecture of the sacrificial layer). In some embodiments, the sacrificial layer design machine generates the expected emissions map by performing a simulation of the sacrificial test IC to predict/ compute the intensity of the light emissions. The process 800 then ends.

Though not illustrated, in some embodiments, the sacrificial layer design machine 110 performing the process 800 produces multiple different sacrificial layer architectures with different input vectors in order to further improve test coverage of the same IC architecture with different expected emissions patterns.

Figure 9:
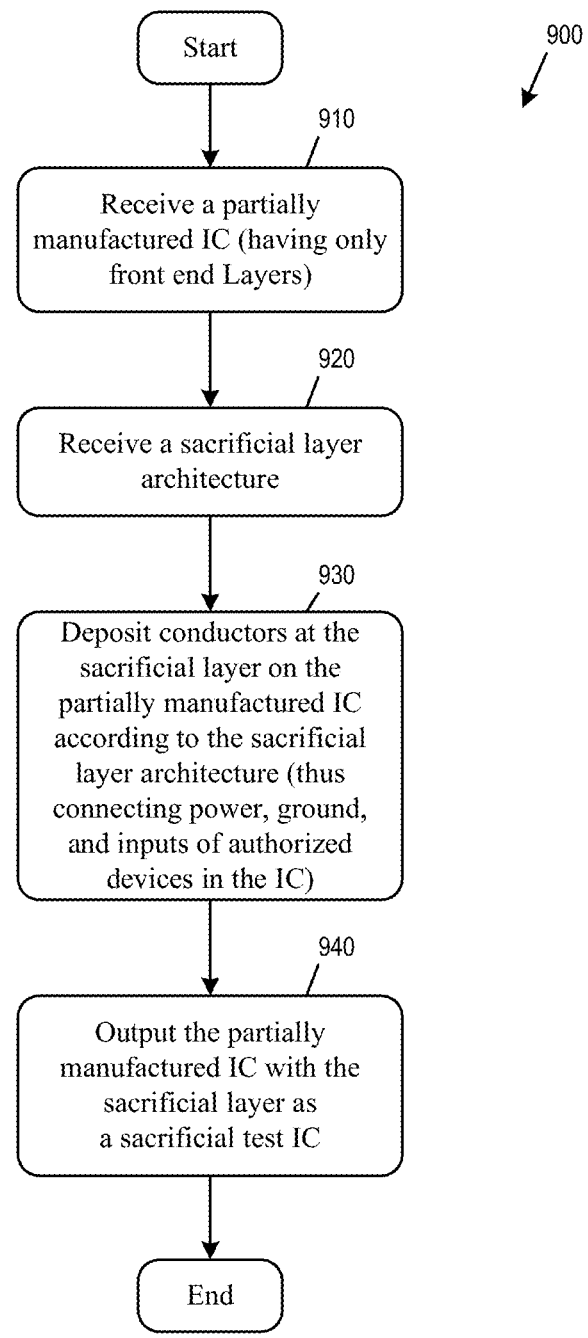
FIG. 9 conceptually illustrates a process for creating a sacrificial test IC having a sacrificial layer, consistent with an exemplary embodiment.

FIG. 9 conceptually illustrates a process 900 for creating a sacrificial test IC having a sacrificial layer, consistent with an exemplary embodiment. In some embodiments, an IC fabrication machine (such as 120) is configured to perform the process 900. In some embodiments, one or more processing units of a computing device controlling the operations of the IC fabrication machine 120 perform the process 900. The creation of a sacrificial test IC is also described in the context of FIGS. 1-3 above.

The IC fabrication machine 120 starts the process 900 when the machine receives (at 910) a partially manufactured IC, i.e., an IC that only has FEOL layers processed at the frontend fab. In some embodiments, the partially manufactured IC is one of the dies on a silicon wafer delivered to the backend fab from the frontend fab. The IC fabrication machine also receives (at 920) a sacrificial layer architecture for the IC.

The IC fabrication machine deposits (at 930) conductors at the sacrificial layer on the partially manufactured IC according to the received sacrificial layer architecture. The deposited conductors electrically connect the power, ground, and inputs of the authorized devices to enable LEOSLC emissions by selected FETs. In some embodiments, the sacrificial layer is processed at the M2 layer. The IC fabrication machine then outputs (at 940) the partially manufactured IC with the sacrificial layer as a sacrificial test IC. The process 900 then ends.

In some embodiments, the IC fabrication machine receives multiple different architectures of the sacrificial layer for a same IC architecture and perform the process 900 to create multiple different sacrificial test ICs to further improved test coverage.

Figure 10:
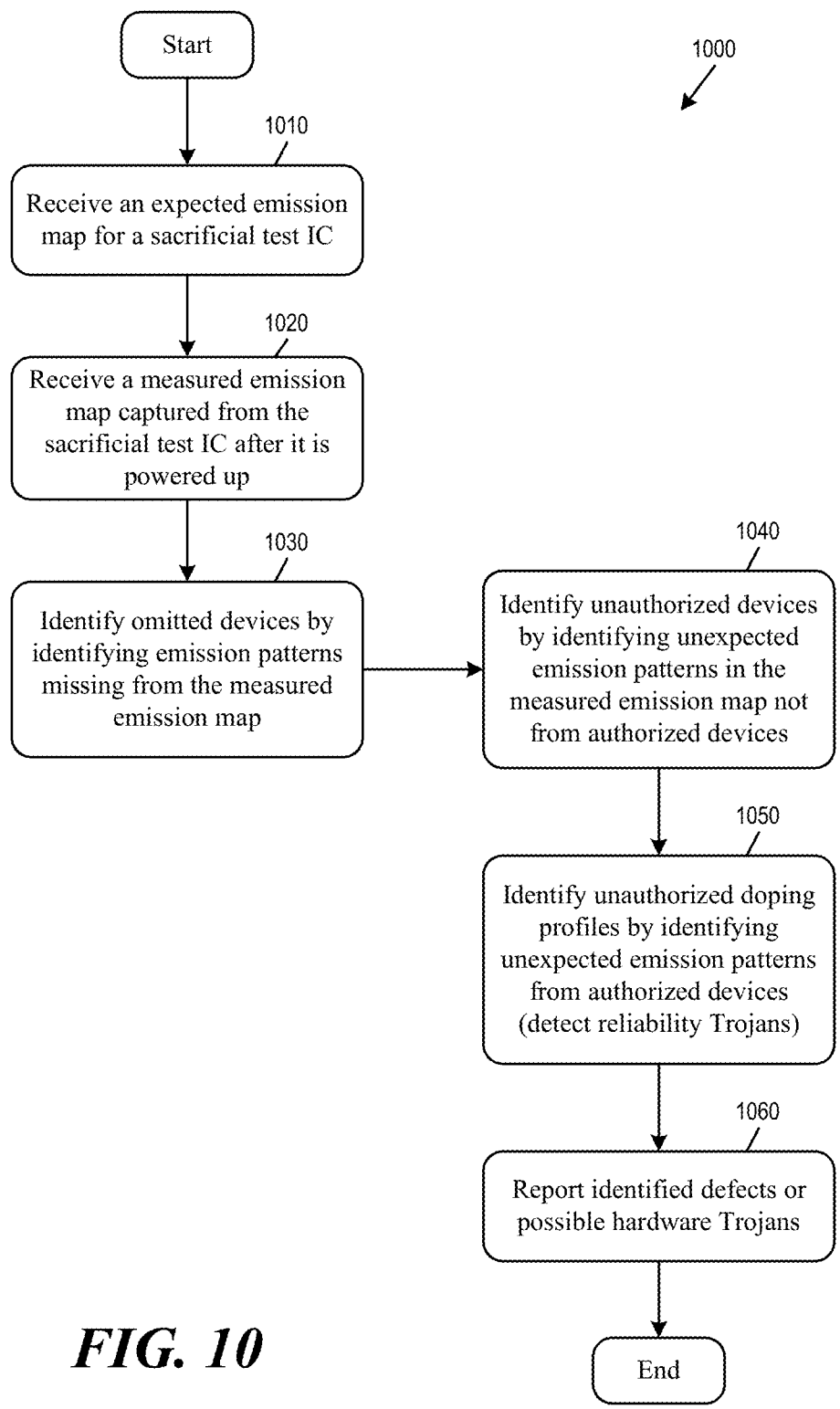
FIG. 10 conceptually illustrates a process for determining whether partially manufactured ICs from a frontend lab have hardware Trojans or other defects by examining the emissions of sacrificial test ICs, consistent with an exemplary embodiment.

FIG. 10 conceptually illustrates a process 1000 for determining whether partially manufactured ICs from a frontend lab have hardware Trojans or other defects by examining the emissions of sacrificial test ICs, consistent with an exemplary embodiment. In some embodiments, one or more processing units of a computing device implementing the defect/Trojan detection machine 140 at the trusted backend fab performs the process 1000. In some embodiments, the computing device that performs the process 800 also performs the process 1000.

The defect/Trojan detection machine receives (at 1010) an expected emissions map for a sacrificial test IC from the sacrificial layer design machine. The defect/Trojan detection machine also receives (at 1020) a measured emissions map based on light emissions captured from the sacrificial test IC (by the emissions capture machine 130) when the sacrificial test IC is powered up.

The defect/Trojan detection machine then compares the measured emissions map and the expected emissions map to identify hardware Trojans and other defects in the IC by performing operations 1030, 1040 and 1050. The defect/Trojan detection machine identifies (at 1030) omitted devices by identifying emissions patterns missing from the measured emissions map when compared with the expected emissions map. The defect/Trojan detection machine identifies (at 1040) unauthorized devices by identifying unexpected emissions patterns in the measured emissions map that are not from authorized devices, i.e., not present in the expected emissions map. Such patterns include LEOSLC emissions due to floating inputs. The defect/Trojan detection machine also identifies (at 1050) unauthorized doping profiles by identifying unexpected emissions patterns due to altered threshold voltage from authorized devices. The identification of hardware Trojans is described in greater detail in the context of FIG. 7 above.

The defect/Trojan detection machine then reports (at 1060) the detected defects or possible hardware Trojans based on the differences between the expected emissions map and the measured emissions map. The operators of the backend trusted fab may use the reported information to decide whether to reject the partially manufactured ICs or to accept the partially manufactured ICs and complete the BEOL fabrication process. The process 1000 then ends.

In some embodiments, the defect/Trojan detection machine uses measured emissions maps from multiple different sacrificial test ICs of the same IC architecture to improve test coverage. Though not illustrated, the defect/Trojan detection machine uses the process 1000 to compare the different measured emissions maps with their respective expected emissions maps to identify hardware Trojans and defects.

Example Electronic System

The present application may be a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. The flowchart and block diagrams in the Figures (e.g., FIGS. 8, 9, and 10) illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 11:
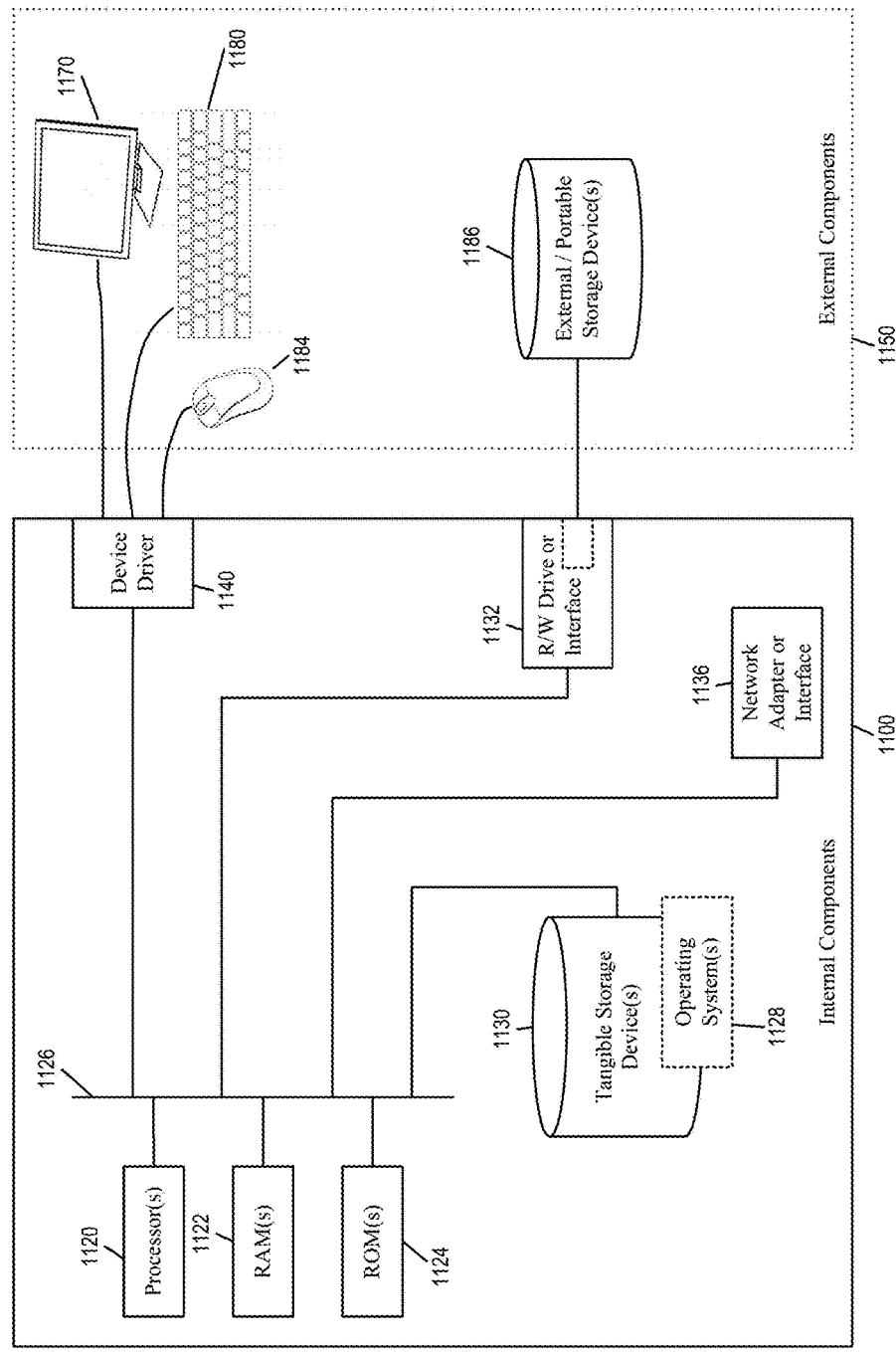
FIG. 11 shows a block diagram of the components of a data processing system in accordance with an illustrative embodiment of the present disclosure.

FIG. 11 shows a block diagram of the components of data processing systems 1100 and 1150 that may be used to implement the sacrificial layer design machine 110 and/or the defect/Trojan detection machine 140 in accordance with an illustrative embodiment of the present disclosure. It should be appreciated that FIG. 11 provides only an illustration of one implementation and does not imply any limitations with regard to the environments in which different embodiments may be implemented. Many modifications to the depicted environments may be made based on design and implementation requirements.

Data processing systems 1100 and 1150 are representative of any electronic device capable of executing machine-readable program instructions. Data processing systems 1100 and 1150 may be representative of a smart phone, a computer system, PDA, or other electronic devices. Examples of computing systems, environments, and/or configurations that may represented by data processing systems 1100 and 1150 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

The data processing systems 1100 and 1150 may include a set of internal components 1100 and a set of external components 1150 illustrated in FIG. 11. The set of internal components 1100 includes one or more processors 1120, one or more computer-readable RAMs 1122 and one or more computer-readable ROMs 1124 on one or more buses 1126, and one or more operating systems 1128 and one or more computer-readable tangible storage devices 1130. The one or more operating systems 1128 and programs such as the programs for executing the processes 800, 900, and 1000 are stored on one or more computer-readable tangible storage devices 1130 for execution by one or more processors 1120 via one or more RAMs 1122 (which typically include cache memory). In the embodiment illustrated in FIG. 11, each of the computer-readable tangible storage devices 1130 is a magnetic disk storage device of an internal hard drive. Alternatively, each of the computer-readable tangible storage devices 1130 is a semiconductor storage device such as ROM 1124, EPROM, flash memory or any other computer-readable tangible storage device that can store a computer program and digital information.

The set of internal components 1100 also includes a R/W drive or interface 1132 to read from and write to one or more portable computer-readable tangible storage devices 1186 such as a CD-ROM, DVD, memory stick, magnetic tape, magnetic disk, optical disk or semiconductor storage device. The instructions for executing the processes 800, 900, and 1000 can be stored on one or more of the respective portable computer-readable tangible storage devices 1186, read via the respective R/W drive or interface 1132 and loaded into the respective hard drive 1130.

The set of internal components 1100 may also include network adapters (or switch port cards) or interfaces 1136 such as a TCP/IP adapter cards, wireless Wi-Fi interface cards, or 3G or 4G wireless interface cards or other wired or wireless communication links. Instructions of processes or programs described above can be downloaded from an external computer (e.g., server) via a network (for example, the Internet, a local area network or other, wide area network) and respective network adapters or interfaces 1136. From the network adapters (or switch port adaptors) or interfaces 1136, the instructions and data of the described programs or processes are loaded into the respective hard drive 1130. The network may comprise copper wires, optical fibers, wireless transmission, routers, firewalls, switches, gateway computers and/or edge servers.

The set of external components 1150 can include a computer display monitor 1170, a keyboard 1180, and a computer mouse 1184. The set of external components 1150 can also include touch screens, virtual keyboards, touch pads, pointing devices, and other human interface devices. The set of internal components 1100 also includes device drivers 1140 to interface to computer display monitor 1170, keyboard 1180 and computer mouse 1184. The device drivers 1140, R/W drive or interface 1132 and network adapter or interface 1136 comprise hardware and software (stored in storage device 1130 and/or ROM 1124).

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computing device comprising:
    a processor; and
    a storage device storing a set of instructions, wherein an execution of the set of instructions by the processor configures the computing device to perform acts comprising:
        receiving an architecture of an integrated circuit (IC) comprising a set of frontend layers and a set of backend layers;
        generating an architecture of a sacrificial layer based on the architecture of the IC, the sacrificial layer specifying power and ground connections to partially constructed devices in a partially manufactured IC that includes the set of frontend layers but not the set of backend layers; and
        generating an expected emissions map by simulating light emissions from the partially constructed devices based on the power and the ground connections provided by the sacrificial layer.

2. The computing device of claim 1, wherein the set of frontend layers comprises a Metal 1 (M1) layer, and the sacrificial layer comprises a Metal 2 (M2) layer.

3. The computing device of claim 1, wherein the partially constructed devices are complementary metal-oxide-semiconductor (CMOS) devices and the light emissions are from off-state leakage current of field effect transistors (FETs).

4. The computing device of claim 1, wherein the architecture of the sacrificial layer further specifies connections for inputs of the partially constructed devices to specific logic levels.

5. The computing device of claim 4, wherein the simulating light emissions from the partially constructed devices is further based on the logical levels of the connected inputs of the partially constructed devices.

6. The computing device of claim 1, wherein the expected emissions map is based on an intensity of the simulated light emissions.

7. The computing device of claim 1, wherein the partially constructed devices have no connection to power or ground without the sacrificial layer.

8. An apparatus configured to perform acts comprising:
    receiving a partially manufactured integrated circuit (IC) that is built according to an IC architecture, the partially manufactured IC includes a set of frontend layers of the IC architecture but not a set of backend layers of the IC architecture;

receiving an architecture of a sacrificial layer;

processing the partially manufactured IC to include the sacrificial layer by providing conducting material according to the architecture of the sacrificial layer to connect partially constructed devices in the partially manufactured IC to power and ground; and outputting the partially manufactured IC with the sacrificial layer as a sacrificial test IC.

9. The apparatus of claim 8, wherein the set of frontend layers includes a Metal 1 (M1) layer, and the sacrificial layer is a Metal 2 (M2) layer.

10. The apparatus of claim 8, wherein the sacrificial test IC does not include the set of backend layers.

11. The apparatus of claim 8, wherein the architecture of the sacrificial layer further specifies connections for inputs of the partially constructed devices to specific logic levels, wherein conducting material further connects the inputs of the partially constructed devices according to the architecture of the sacrificial layer.

12. The apparatus of claim 8, wherein the partially constructed devices have no connection to power or ground without the sacrificial layer.

13. The apparatus of claim 8, wherein the sacrificial test IC comprises no processing layer above the sacrificial layer.

14. A computer-implemented method comprising:

receiving a measured emissions map based on light emissions captured from a sacrificial test IC, the sacrificial test IC being a partially manufactured IC including a set of frontend layers of an IC architecture but not a set of backend layers of the IC architecture, the sacrificial test IC further comprising a sacrificial layer for powering devices in the partially manufactured IC without the set of backend layers;

receiving an expected emissions map for the sacrificial test IC; and comparing the measured emissions map and the expected emissions map to identify deviations from the IC architecture in the frontend layers.

15. The computer-implemented method of claim 14, wherein the set of frontend layers includes a Metal 1 (M1) layer, and the sacrificial layer is a Metal 2 (M2) layer.

16. The computer-implemented method of claim 14, wherein:

the light emissions are captured from complementary metal-oxide-semiconductor (CMOS) devices in the sacrificial test IC, and the light emissions are from off-state leakage current of field effect transistors (FETs).

17. The computer-implemented method of claim 14, wherein the sacrificial layer further connects inputs of the devices in the partially manufactured IC to specific logic levels without the set of backend layers, wherein the expected emissions map is generated based on the specific logic levels of the inputs of the devices.

18. The computer-implemented method of claim 14, wherein identifying deviations from the IC architecture comprises identifying omitted devices by identifying emissions patterns missing from the measured emissions map.

19. The computer-implemented method of claim 14, wherein identifying deviations from the IC architecture comprises identifying one or more unauthorized devices by identifying unexpected emissions patterns in the measured emissions map that are not from authorized devices.

20. The computer-implemented method of claim 14, wherein identifying deviations from the IC architecture comprises identifying one or more unauthorized doping profiles by identifying unexpected emissions patterns from authorized devices.

* * * * *